United States Patent [19]

Pikulik

[11] Patent Number: 4,880,499
[45] Date of Patent: Nov. 14, 1989

[54] METHOD FOR MEASUREMENT OF THE PERMEABILITY TO WATER

[75] Inventor: Ivan I. Pikulik, Pointe Claire, Canada

[73] Assignee: Pulp and Paper Research Institute of Canada, Pointe Claire, Canada

[21] Appl. No.: 49,250

[22] Filed: May 13, 1987

[30] Foreign Application Priority Data

May 20, 1986 [CA] Canada .................................. 509566

[51] Int. Cl.$^4$ ............................................. D21F 1/32
[52] U.S. Cl. ...................................... 162/198; 73/38; 162/263; 162/275
[58] Field of Search ............... 162/198, 263, 275, 278; 73/38

[56] References Cited

U.S. PATENT DOCUMENTS

| | | | |
|---|---|---|---|
| 3,499,315 | 3/1970 | Marino | 73/38 |
| 3,577,767 | 5/1971 | Stedile | 73/38 |
| 3,762,211 | 10/1973 | Poulsen | 73/38 |
| 4,385,517 | 5/1983 | Source et al. | 73/38 |
| 4,401,147 | 8/1983 | Beck et al. | 162/263 |

FOREIGN PATENT DOCUMENTS 2061341  5/1981  United Kingdom ............... 162/277

*Primary Examiner*—Steve Alvo
*Attorney, Agent, or Firm*—Lawrence I. Field

[57] ABSTRACT

A method for measuring the permeability of pervious sheet material is disclosed; the measurement is based on the flow rate of water ejected at a given pressure between 2 and 1000 kPa through a nozzle pressed against one surface of the sheet material whose permeability is to be measured.

4 Claims, 1 Drawing Sheet

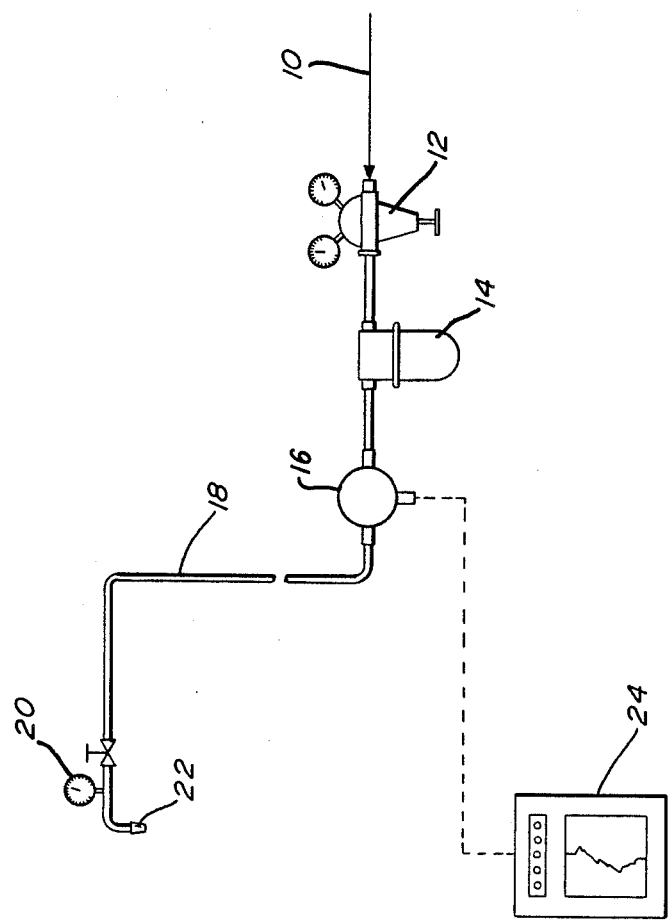

METHOD FOR MEASUREMENT OF THE PERMEABILITY TO WATER

The present invention relates to a method and apparatus for measuring the permeability of a pervious sheet material.

It is often desired to measure the water permeability of a flexible pervious sheet material such as is used in paper-making equipment. There are several instruments presently commercially available and generally, they utilize a measurement of the air flow rate through the sheet material with a very small difference in air pressure on the opposed surfaces of the sheet material. Reference may be had to U.S. Pat. Nos. 2,722,837; 3,091,123; and 3,397,319 which teach such instruments.

One such instrument presently used in the papermaking industry measures the flow of air through a header which is held firmly in contact with a felt or forming fabric. The driving force for the air flow is an air pressure differential of 0.12 kPa which is supplied to the header as a positive pressure or a vacuum. Generally, these types of instruments are portable and can be used to measure the permeability profile of the sheet material in the cross machine direction while the paper machine is running.

Other machines are known wherein the sheet material must be clamped on both sides and accordingly cannot be used for measures in dynamic conditions. However, all such instruments are generally characterized in that a very low pressure differential is utilized. While the various instruments differ in the area of the contact established between the header and measured material, and in the complexity of the instrumentation employed, they all measure permeability of the sheet material to air at very low pressure differentials. One of the problems which has been encountered with such instrumentation is the poor reproducibility of the permeability measurement. Even a small deviation from the right angle between a hand held probe and a fast running sheet material results in an incorrect reading.

It is therefore an object of the present invention to provide a method and apparatus for the measurement of the water permeability of a pervious sheet material.

In one aspect of the invention, there is provided a method for the measure of the permeability of pervious sheet material which includes the steps of placing a nozzle against one surface of the sheet material, causing water to flow through the nozzle at a pressure of between 2 kPa and 1000 kPa, and measuring the rate of flow of the water.

There is also provided an apparatus for the measurement of water permeability of a pervious sheet material which comprises a nozzle, a regulator and indicator of water pressure, a water flow rate gauge. The system or apparatus may include accessories such as a high pressure water pump, a filter, data recording system, a device for scanning the sensor across the machine, etc.

Permeability is one of the critical properties of paper machine textiles. For example, as about 100 tons or more of water are removed through the forming fabric for every tonne of paper produced it is important that the fabric offers little resistance to the water flow. Additional water is then removed by an intensive mechanical compression of wet paper against a felt in the nips of a wet press. For a good performance of the wet press it is essential that the felt remain permeable to water even when compressed by loads which on the conventional presses range from about 30 to 350 kN/m. A low felt permeability results in an inadequate water removal from the sheet, which can lead to crushing of paper by the compressed water accumulated in the press nip, breaks of the sheet, slow drying of paper and might force a reduction in the speed of a paper machine. Humid paper leaving the press section of a paper machine is dried while it is pressed by the dryer fabric on the surface of a series of rotating steam-heated dryer cylinders. The dryer fabric must allow an easy transverse ventilation which conveys the dry air towards the heated paper and carries the humid air out of the system.

The permeability of press felts as well as that of new forming and dryer fabrics is an important part of the product specification and frequently serves users as a criterion for selection of a suitable product.

Even if material with the correct permeability is installed on a paper machine, its permeability continuously changes and usually declines during its lifetime as a result of deposition of materials such as pitch or fibres, and in the case of press felts, also as a result of an irreversible mechanical compaction. To slow down the loss of permeability most users clean the paper machine fabrics continuously or periodically by high pressure water jets or by other means. When the permeability drops below a certain critical value the fabrics especially the press felts, might need to be removed (I. I. Pikulik and R. G. Batty, 1984 Annual Meeting CPPA/TS, Preprints B303). Thus measurement of the permeability of the running fabric provides information about an important process criterion, and also serves for evaluation of the cleaning procedure and determination of the life of the fabric.

The instruments presently used for measurement of permeability of paper machine fabric measure the flow of air through the fabric at a pressure differential of about 0.1 kPa. While measurements conducted in this manner might give useful results for dryer fabrics, they are completely inadequate and, in fact, might be misleading if applied to forming fabric and especially to press felts.

Both the forming fabric and press felts contain a considerable amount of water during the operation of the paper machine. For example, the water content of more than 50 press felts which we measured on 22 paper machines ranged from less than 50% to more than 100% based on the weight of dry felts. A similar proportion of water can also be found in the wet forming fabrics. It is clear that a large portion of the voids within the felt or the fabric running on a paper machine is filled by water. The residence time of the clothing over the sensor of the presently used permeability tester depends on the machine and might have values ranging from less than 3 to about 30 milliseconds. The air pressure differential of about 0.1 kPa used by the presently-used permeability tester is too low to remove, in the short time available, water held by capillary forces in the clothing. Therefore, the permeability measured in this manner is strongly affected by the moisture content of the medium and since the moisture is added to or removed from the felts and fabrics as they proceed on the paper machine, different values of the permeability can be measured at different positions along the felt or fabric loop. The felts and fabrics saturated with water, which display a low permeability for air at low pressure, might still have a good permeability to water at such pressures as occur in the press nips or forming zones respectively.

The method for measurement of permeability of sheet-forming materials which is the subject of this invention is based on measurement of the flow of water which is forced into the measured medium at a pressure similar to that experienced by the material during its application. Water pressure range from 2 to 1000 kPa but values close to 700 kPa were found convenient for measurement of the permeability of press felts and values close to 3 kPa were convenient for measurements on forming or dryer fabrics.

Having thus generally described the invention, reference will be made to the accompanying drawing illustrating an embodiment thereof, in which:

FIG. 1 is a schematic diagram of an apparatus for the measurement of permeability of a pervious sheet material.

As shown in FIG. 1, a typical system for the measurement of the permeability of a pervious sheet material may include a high pressure water source 10 connected to a suitable pressure regulator 12. A strainer 14 may be provided on the line and a suitable flow meter 16 to measure the rate flow of the water is provided. On the output side of the flow meter, there may be provided a high pressure flexible tube 18 having a nozzle 22 at the end thereof. Nozzle 22 is preferably quickly interchangeable with different size nozzles as may be required. For the convenience of the operator, a suitable pressure indicator 20 may be located near the nozzle. If desired, and as shown in FIG. 1, a flow indicator recorder 24 may be provided to keep a suitable record of flow rates over a desired period of time.

The nozzle may be of a convenient size and typically, in diameter in the order of between 1-4 mm would be suitable. Naturally, the flow of water is constant from the regulator and all tubes and nozzles have smooth walls to minimize turbulence and variations.

The permeability of the pervious sheet material would then be reported as the water flow at a specified pressure through a specified nozzle into the sheet material. The contact between the nozzle and the material can be established by hand or by suitable mechanical nozzle holder. The measurements can be carried out at selected spots or the nozzle can be continuously shifted across the machine to obtain a cross machine permeability profile.

The following examples illustrate the use of a method and apparatus of the present invention.

EXAMPLE 1

A pilot paper machine was producing newsprint with a basis weight of 48 g/m$^2$ at a speed of 800 m/min. A DUROFLO$^{(Trademark)}$ felt supplied by Albany International Canada Inc. was used as a pick-up felt and also first felt of a three-roll inclined press. The first press nip was of a suction type and operated at a load of 45 kN/m. The permeability of the first felt, which was not conditioned during the trial, was frequently measured with a currently available instrument as discussed above, and the felt moisture content was measured with a SCAN-PRO$^{(Trademark)}$ felt moisture meter. During the trial the moisture content of paper entering the press section was gradually increased, which resulted in an increased felt moisture content. The felt permeability measured by the conventional method decreased from values close to 50 ft$^3$/ft$^2$/min at a felt moisture content of 550 g water/m$^2$ to some 5 ft$^3$/ft$^2$/min at 900 g water/m$^2$.

Experience has shown that felt with permeabilities below 10 ft$^3$/ft$^2$/min do not perform adequately in the first position of the pilot machine. In the present trials, however, the felt performed flawlessly and the moisture content in the paper leaving the first press nip remained constant at 33.8% as the permeability decreased from 48 ft$^3$/ft$^2$/min to 5 ft$^3$/ft$^2$/min. The measured decrease in the felt permeability reflected an increase in the felt moisture rather than a compaction filling or a similar change in the felt structure. Since the moisture content of the paper entering the press section increased from 83.8% at the felt permeability of 48 ft$^3$/ft$^2$/min to 90.2% at the felt permeability of 5 ft$^3$/ft$^2$/min and since the moisture content of the paper leaving the press nip remained constant, one arrives at a paradoxical conclusion that the felt removed large amounts of water in the situation when its permeability measured by the conventional method was lowest. Furthermore, when the moisture content of the paper entering the press section was reduced, the felt moisture content also decreased and the felt permeability measured by the conventional method increased. This example indicates shortcomings of the previous methods used for measurement of felt permeability.

EXAMPLE 2

With the press section of the pilot paper machine operating at 800 m/min the moisture content of the first felt was varied from 600 to 1000 g/m$^2$ and that of the second felt from 460 to 730 g/m$^2$. This variation in moisture was achieved by adjusting the water flow through the cleaning shower and the load of press nips. The permeability of both felts was measured at 14 conditions of the felt moisture content with a conventional instrument and with the prototype of the instrument of the present invention. The permeability of both felts recorded with our instrument remained constant throughout the trial at 1.60 L/min for the first felt and 0.84 L/min for the second felt when the water pressure used was 700 kPa and the diameter of the nozzle was 2.5 mm. The air permeability of the felts changed with their moisture contents: the first felt permeability was zero at a moisture level of 1000 g/m$^2$ and 32 ft$^3$/ft$^2$/min at 600 g/m$^2$; the second felt had a zero permeability at a moisture of 730 g/m$^2$ and a permeability of 28 ft$^3$/ft$^2$min was measured when the moisture was decreased to 460 g/m$^2$. These measurements were repeatable. Clearly the permeability to water of the felts did not measurably change during the short trial and the measurement of felt permeability with a conventional instrument did not provide a correct image of felt behaviour in the press nip. This demonstrates the superiority of the invented method of porosity measurement over the conventional method.

It will be understood that the above described embodiments are for purposes of illustration only and that changes and modifications may be made thereto.

The embodiments of the invention in which an exclusive property or privilege is claimed are defined as follows:

1. A method for the measuring of the water permeability of a pervious sheet material in a paper making machine while said machine is running, wherein the measuring being of the water flow at a specified pressure through a specified nozzle into the sheet material which comprises the steps of:

placing said nozzle against and substantially normal to a single surface of said sheet material while said sheet material is running through said machine, forcing a flow of water into said running sheet material and through said nozzle at a specified pressure of between 2 kPa and 1,000 kPa, and measuring the water permeability of said sheet material by measuring the rate of flow of the water through said nozzle and into said sheet material while said sheet material is running through said machine.

2. The method of claim 1 wherein said pervious sheet material is a felt material.

3. The method of claim 1 wherein the specified pressure is approximately 700 kPa and said sheet material is a press felt.

4. The method of claim 1 wherein the specified pressure is approximately 3 kPa and said sheet material is a forming or dryer fabric.

* * * * *